US008287818B2

(12) United States Patent
Kantrowitz et al.

(10) Patent No.: US 8,287,818 B2
(45) Date of Patent: Oct. 16, 2012

(54) MODULAR HOSPITAL CART

(76) Inventors: Allen B. Kantrowitz, Williamstown, MA (US); In K. Mun, Nanuet, NY (US)

( * ) Notice: Subject to any disclaimer, the term of this patent is extended or adjusted under 35 U.S.C. 154(b) by 1766 days.

(21) Appl. No.: 11/488,418

(22) Filed: Jul. 18, 2006

(65) Prior Publication Data

US 2007/0014693 A1 Jan. 18, 2007

Related U.S. Application Data

(60) Provisional application No. 60/700,097, filed on Jul. 18, 2005.

(51) Int. Cl.
*G01N 33/00* (2006.01)

(52) U.S. Cl. .......................... 422/500; 422/50; 422/68.1

(58) Field of Classification Search .................... 422/50, 422/68.1, 500
See application file for complete search history.

(56) References Cited

U.S. PATENT DOCUMENTS

| | | | | |
|---|---|---|---|---|
| 5,133,935 | A * | 7/1992 | Copelan | 422/430 |
| 6,971,506 | B2 | 12/2005 | Hassinen et al. | |
| 7,070,053 | B1 | 7/2006 | Abrams et al. | |
| 7,083,106 | B2 | 8/2006 | Albany | |
| 7,164,353 | B2 | 1/2007 | Puleston et al. | |
| 7,175,081 | B2 | 2/2007 | Andreasson et al. | |
| 7,178,416 | B2 | 2/2007 | Whelan et al. | |
| 7,179,424 | B2 | 2/2007 | Williamson, IV et al. | |
| 2003/0174046 | A1 | 9/2003 | Abrams | |
| 2003/0183683 | A1 | 10/2003 | Stewart | |
| 2004/0129769 | A1 | 7/2004 | Kovach | |
| 2005/0091896 | A1 | 5/2005 | Kotik et al. | |
| 2005/0132775 | A1 | 6/2005 | Laugharn et al. | |
| 2005/0136548 | A1 | 6/2005 | McDevitt et al. | |
| 2006/0102584 | A1 | 5/2006 | Wellman | |
| 2006/0210447 | A1 | 9/2006 | Hunsley | |
| 2007/0028495 | A1 | 2/2007 | Kotik et al. | |
| 2007/0028642 | A1 | 2/2007 | Glade et al. | |
| 2007/0036686 | A1 | 2/2007 | Hatamian et al. | |

* cited by examiner

*Primary Examiner* — Sam P Siefke

(74) *Attorney, Agent, or Firm* — Patent Procurement Services

(57) ABSTRACT

Improved systems and methods are provided for monitoring compliance with an order for a patient specimen. Broadly, an inventive system incorporates a machine readable wireless identification and sensor technology to provide feedback to a caregiver regarding compliance with a specimen order. In particular, a system for monitoring compliance with an order for a specimen is provided which includes a specimen container having an attached machine readable wireless tag. The tag contains specimen container characteristic information. The tagged container aids in indicating to a user whether the correct specimen container type has been chosen. Further, a system is provided which includes a sensor useful in indicating whether a sufficient quantity of specimen has been obtained in order to perform the requested laboratory test as part of the patient's care.

17 Claims, 2 Drawing Sheets

MODULAR HOSPITAL CART

RELATED APPLICATION

This application claims priority of U.S. Provisional Patent Application Ser. No. 60/700,079 filed Jul. 18, 2005, which is incorporated herein by reference.

FIELD OF THE INVENTION

The invention relates to management of patient care and systems and methods designed for use in minimizing non-compliance with an order for a patient specimen. In particular, the invention relates to systems and methods for monitoring compliance with an order for a patient specimen.

BACKGROUND OF THE INVENTION

Obtaining a patient specimen which complies with a physician order for the specimen is of considerable importance in efficient patient care. For example, a particular blood test may require that the blood specimen be placed in a tube containing an anticoagulant. In addition, some laboratory tests require a specified amount of a specimen in order to perform the test correctly. If such requirements are disregarded, further specimens must be collected, with consequential delay in obtaining test results. Since time is of the essence in many medical situations, it is desirable to communicate any special requirements involved in obtaining a specimen clearly so as to obtain the correctly handled specimen in a timely manner. Further, it would be especially desirable to be alerted to the fact that a specimen has been incorrectly obtained as soon as possible in order to avoid delay.

Thus, an improved system and method for monitoring compliance with an order for a patient specimen is needed.

SUMMARY OF THE INVENTION

A system for monitoring compliance with an order for a specimen is provided which includes a specimen container having an attached machine readable identification tag containing specimen container characteristic information. Specimen container characteristic information includes such information as a specimen container type, container identification information, weight of the container when empty, weight of the container containing a volume of specimen, opacity of the container, opacity of the container containing a volume of specimen, patient identification information identifying a patient whose specimen is to be contained in the specimen container, a test to be performed on the specimen, and an amount of specimen required. Further included in an inventive system is a device having data input and output capacity, processing circuitry, memory circuitry and an executable program for analysis of data transmitted from the tag, a tag reader in data communication with the tag and the device, and a display disposed on the device or the reader.

Optionally included in an inventive system is a specimen container holder having a receptacle for removably receiving a specimen container.

Also optionally included in an inventive system is a sensor, such as a sensor for sensing a quantity of specimen in a container, disposed in contact with the holder receptacle. Such a sensor is preferably in data transmission communication with the device so as to transmit a sensor signal to the processing and memory circuitry. A system including a sensor further includes an executable program for analysis of data transmitted from the sensor. Optionally, a sensor for sensing a quantity of specimen in a container is a weight sensor or an opacity sensor.

In one embodiment, the reader is disposed on the device having the processing and memory circuitry.

Optionally, a patient identification badge having an attached wireless machine readable identification tag is included in an inventive system.

Processes for monitoring compliance with an order for a specimen are provided by the present invention which include the steps of providing a system as described herein and placing an order for a patient specimen which requires use of a specific type of specimen container in order to comply with the order. The order is preferably input into the system such that a record of the order is created in memory circuitry. The record may be associated with a reference database having records of laboratory test requirements. A further step includes selection of a specimen container and activation of the radio frequency reader to read the tag attached to the specimen container. The tag contains information indicative of the container type which is read by the reader and transmitted from the reader to the device having data input and output capacity, processing circuitry, memory circuitry and an executable program for analysis of data transmitted from the tag. In a further step the record of the order for a patient specimen requiring use of the first type of specimen container is retrieved and compared with the information sent from the tag reader identifying the container type. The comparison yields information about whether the chosen specimen container type is the type of specimen container required in order to comply with the order. This information is presented on the display to indicate to a user whether the specimen container having the attached tag read by the reader is the first type of specimen container required in order to comply with the order, thereby monitoring compliance with an order for a specimen.

An optional step of an inventive process is that of confirming the identity of the patient as a patient for whom the order for a patient specimen was placed.

Further provided by the invention is a process for monitoring compliance with an order for a specimen that includes the steps of providing a system as described herein including a sensor disposed on a container holder and entering an order for a patient specimen to the memory of a device having data input and output capacity, processing circuitry, memory circuitry and an executable program for analysis of data transmitted from the sensor. The order for a patient specimen requires a specified quantity of a patient specimen in order to comply with the order in this embodiment. In a further step a quantity of a patient specimen is obtained from a patient and the quantity of the specimen is placed in the specimen container.

The specimen container having the quantity of the patient specimen is received in a receptacle of the specimen container holder, the receptacle having a sensor for measuring the quantity of the patient specimen disposed thereon. A sensor signal is transmitted from the sensor to the device having data input and output capacity, processing circuitry, memory circuitry and an executable program for analysis of data transmitted from the sensor. In addition the record of the order for a patient specimen requiring the specified quantity of a patient specimen in order to comply with the order is retrieved and compared with information transmitted by the sensor indicative of the quantity of specimen in the container. The comparison generates information regarding whether the quantity of specimen in the container is sufficient in order to comply with the order for the specified quantity of a patient specimen.

This information is presented by the display, indicating whether the quantity of specimen in the container is sufficient in order to comply with the order, thereby monitoring compliance with an order for a specimen. Optionally, a step of confirming the identity of the patient as a patient for whom the order for a patient specimen was placed is included. Further optionally, the reader is activated to read the information contained in the tag attached to the specimen container and this information or a portion thereof is recorded and/or processed and associated with an indication that the required specimen has been obtained as required to comply with the order.

DETAILED DESCRIPTION OF THE INVENTION

Figure 1:
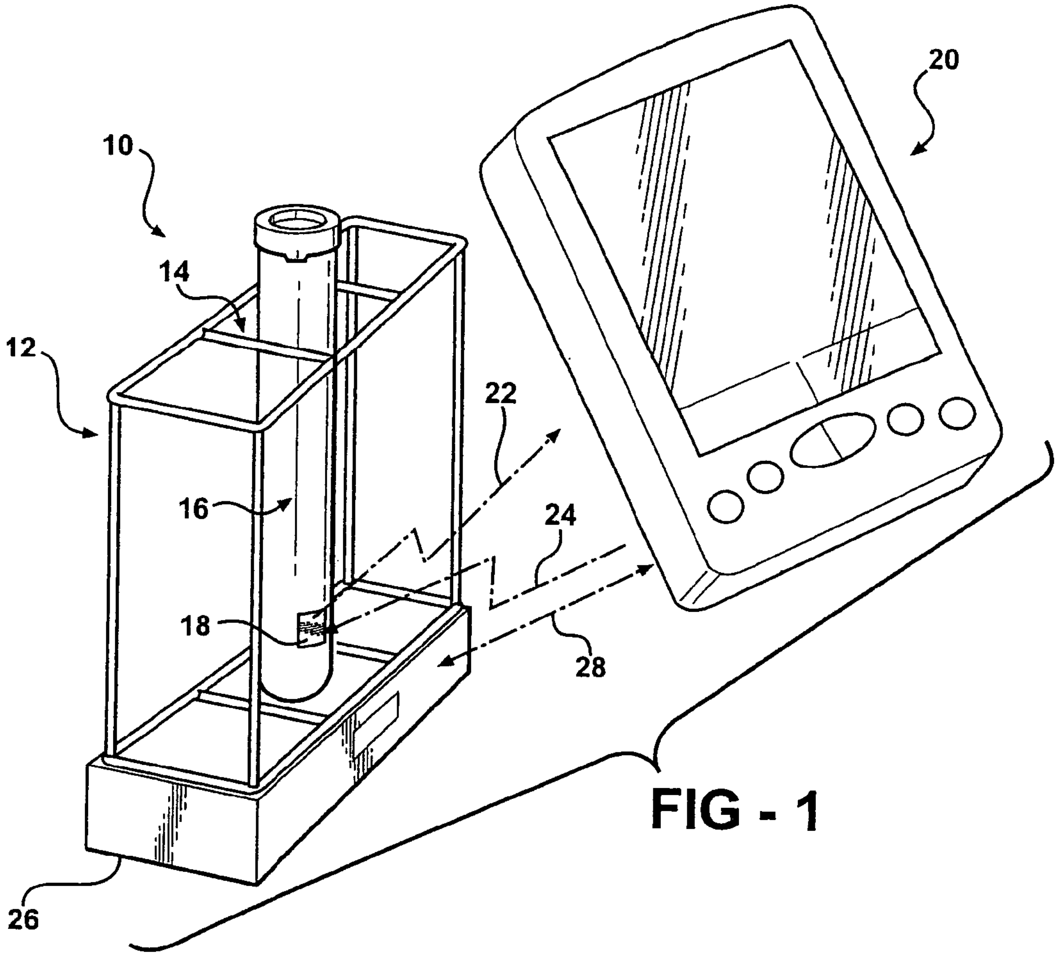
FIG. 1 is a drawing illustrating an embodiment of the invention.

Improved systems and methods are provided for monitoring compliance with an order for a patient specimen. Broadly, an inventive system incorporates a machine readable wireless identification and optional sensor technology to provide feedback to a caregiver regarding compliance with a specimen order.

As used herein a machine readable wireless identification tag is defined to include a radio frequency identification (RFID) tag, one-dimensional or two-dimensional barcode.

An inventive system includes a specimen container having an attached machine readable wireless tag, and a radio frequency identification reader configured to transmit an interrogation signal and receive responsive data from the tag. Also included is a device having data input and output capacity, a display, and processing and memory circuitry along with an executable program for analysis of data transmitted from the tag. Optionally, an inventive system further includes a specimen container holder having a receptacle for removably receiving a specimen container. Also optionally, an inventive system further includes a sensor for detecting the quantity of a specimen in a container, the sensor disposed in contact with the receptacle. In a further option, a patient identification badge having an attached radio frequency identification tag is provided for use in an inventive system.

In operation, a particular embodiment of an inventive system for monitoring compliance with an order for a patient specimen is used when an order for a laboratory test is given by a physician or other caregiver. Information regarding the order and patient are input to processing and memory circuitry included in a device or accessible by the device as described herein to create a record of the order. The record of the order includes or is linked to a record of requirements that must be fulfilled to comply with the order. For example, an order for a laboratory test to measure potassium in a patient's blood is given by a physician. Information such as the name of the patient, the name or identification number of the ordering physician and the name or identification number of the test ordered are input to processing and memory circuitry included in a device or accessible by the device as described herein to create a record of the order. The name or ID number of the particular blood test may be associated with information in a stored record of requirements necessary to comply with the particular test order. For example, input of "serum potassium level" or an ID number signifying such a test may be linked in a database to requirements necessary to comply with the order such as "5 mL blood sample needed" and/or "red top vacutainer tube required as sample container."

A technician is dispatched to acquire the specimen from the patient. The technician inputs a directive to a device to access the record or part of the record of the order for the specimen. The record or part of the record may be presented to the technician in any of various ways, such as a visual presentation of patient name, specimen type required, and/or specimen container required on a display. The technician preferably confirms the identity of the individual from whom the specimen is obtained. For example, in a preferred option, the technician uses an RFID reader to read an RFID tag attached to an identification badge worn by an individual in order to confirm that the individual is the patient from whom the specimen is to be obtained. Systems and methods including such an identification badge are described in applications for U.S. patent entitled "Associated Patient Care Items" and "Auto ID System for Medical Care Setting," both filed Jan. 21, 2004, which are hereby incorporated by reference in their entirety.

The specimen container holder may be used to carry specimen containers both before and after filling with specimen. The technician takes a specimen container and presents the container tag to a reader for reading of the tag information. Optionally, the specimen container holder is configured such that placement of a tagged container in a receptacle activates the reader to read the tag.

A machine readable wireless tag contains information regarding a specimen container characteristic as described further below. The reader is activated such that the reader transmits an interrogation signal to the tag and the reader receives information associated with the tag. Tag information received by the reader is transmitted to processing and memory circuitry included in the device operative to compare the tag information with the record of the container type required by the order. A signal is presented to the technician indicative of correct or incorrect choice of specimen container necessary to comply with the order. In the case of an incorrect choice of container, visual display of correct instructions is optionally presented to the technician. Further optionally, a record is made of information relating to the reading of the tag, such as time and date of the read. Following placement of the specimen in the specimen container, the filled specimen container is optionally presented to the reader for tag reading. The technician may provide an input to the device indicating that the specimen has been acquired, and time, date and unique container identification information may be recorded.

In an embodiment in which a sensor for measuring a quantity of a specimen is included in an inventive system, the technician places the specimen container having a quantity of specimen in a receptacle of the specimen container holder. The sensor disposed on the receptacle is operative to sense a characteristic of the specimen in the container indicative of the quantity of the specimen in the container. A sensor signal is transmitted to the processing and memory circuitry and the included executable program for analysis of data transmitted from the tag and sensor. The amount of specimen in the container is compared with the amount of specimen required to comply with the order for the specimen and feedback regarding compliance with the requirements is presented to the technician via the display along with optional further instructions.

As noted, a machine readable wireless identification tag attached to a specimen container included in an inventive system preferably contains information regarding the type of container to which the tag is attached. For example, the tag contains information such as the type of container, container volume, container weight when empty, container weight when a particular volume of specimen is placed in the container, opacity of the container wall when empty, opacity when a particular specimen is placed in the container, and a container identification number. The radio frequency identification tag may further contain information regarding the patient from whom the specimen is obtained.

Various types of machine readable wireless tag and reader combinations may be used in an inventive system and method. In one embodiment, the tags are RFID passive tags, those that transmit information only in response to interrogation by a reader. In general, a passive tag is energized to transmit identification information by the reader. Passive tags may include an energy source, such as a battery, for example to increase read range. Such tags are often termed semi-passive or battery-assisted passive. In another embodiment, the tags are RFID active tags and may initiate information transmission. Active tags are powered by an energy source, such as a battery, and may transmit continuously or intermittently. Numerous radio frequency identification readers and tags have been developed illustratively including those described in U.S. Pat. Nos. 4,442,507; 4,796,074; 5,095,362; 5,296,722; 5,347,263; 5,347,280; 5,378,880; 5,407,851; 5,430,441; 5,528,222; 5,550,547; 5,521,601; 5,541,604; 5,565,846; 5,682,143; and 5,625,341.

In one embodiment, the radio frequency tags are read-only or barcodes. Such RFID tags are known in the art and are exemplified by the "ES600-Series Read Only Tags" commercially available from Escort Memory Systems (EMS), Scotts Valley, Calif. Alternatively, tags are configured to allow information to be written to the tag. For instance, the patient's name, address, hospital ID and/or medical information may be written to the machine readable wireless tags. Read-write RFID tags are known in the art and include IntelliTag Series from Intermec Technologies Corporation and the HMS-100 Series passive read-write tags available from EMS.

A machine readable wireless tag reader is included in an inventive system which is configured to interrogate the tag and receive information from the tag. The reader is in data communication with a device having input and output capacity, processing and memory circuitry, along with an executable program for analysis of data transmitted from the tag. Exemplary devices include a personal digital assistant, personal computer or mainframe computer. Optionally, the device is portable. The reader may be in wireless or direct wired connection to the device for communication of data. In addition, information received from the tag may be input from an RFID reader over a wired or wireless connection to a device such as a server or computer network accessible by multiple users from multiple locations. The server may be any type of computer system such as a personal digital assistant, personal computer, workstation or mainframe computer.

Optionally, a reader is directly incorporated in a device including processing and memory circuitry as described above. Such devices illustratively include an RFID reader with database and processor components, a personal digital assistant having a reader capability or personal computer having reader capability.

A display included in an inventive system is operative to present a user with information relative to the specimen. For example, the display is operative to present a visual or acoustic signal to a user. The display is preferably attached to the device and/or the reader. A display illustratively includes a display screen, a light signal emitter, such as an LED, and an acoustic signal emitter.

A user input device is any of various known in the art illustratively include a pushbutton, a touch-activated screen, a mouse, a keyboard and the like.

In a preferred embodiment, a memory component of electrical circuitry included in an inventive system includes a database for storing information relating to a particular order for a specimen. For example, when an order for a specimen is placed by a physician or other caregiver, information such as the date and time of order placement, the test to be performed on the specimen, name of the person ordering the specimen and time and date that the specimen must be obtained, and the name of the person to whom test results should be sent, may be entered into a database. Other information generally relating to orders for particular types of tests, such as container type required, specimen amount required and storage conditions required, may be entered into the database or retrieved by processing circuitry from a reference database, the reference database containing requirements relating to all or a subset of tests which may be ordered in a particular hospital or medical treatment setting implementing an inventive system.

An inventive system includes a specimen container holder having a receptacle for removably receiving a specimen container. A specimen container holder is optionally a standalone object having one or more receptacles for a specimen container. In a further option, a specimen container holder is attached to another element of an inventive system. For example, in one embodiment, a specimen container holder has an attached to a wireless machine reader. In another exemplary embodiment, a specimen container holder is attached to a device having processing and memory circuitry, such as a personal digital assistant (PDA), which optionally incorporates a reader. In a preferred option, a visual display device is included as part of the reader and/or device including the processing and memory circuitry, such as a PDA.

A visual display is activated in response to commands from processing circuitry to present a signal to a user. A signal presented to a user may be in the form of a text message, colored and/or flashing light, and/or an audio cue, such as a warning tone. A signal is activated to alert a user and/or prompt user action. A signal is may be configured to indicate that an adequate specimen amount has been obtained, an inadequate specimen amount has been obtained, further specimens from this patient remain to be obtained, all required specimens have been obtained, extra specimens have been obtained, a mismatch between the type of tube used and the like.

A receptacle of a specimen container holder is configured to securely support a specimen container to ensure against breakage or loss of the specimen container.

Optionally, a patient identification badge having an attached radio frequency identification tag is included in an inventive system. Such a badge is typically worn by the patient and the tag attached to the badge contains information identifying the patient. Reading the tag attached to the identification badge allows a reader user to confirm the identity of the patient, for instance, prior to obtaining a specimen from the patient.

A preferred embodiment of an inventive system further includes a specimen sensor attached to a holder receptacle such that receiving a specimen container therein generates a sensor signal. The specimen sensor is in data communication with processing and memory circuitry included in an inventive system. In such an embodiment, a program for analysis of data transmitted from the sensor and the tag executable by the processing and memory circuitry is included in an inventive system.

In such an embodiment, a specimen sensor is configured to generate a sensor signal indicative of a characteristic of the specimen container received in the receptacle. The sensor is adapted to transmit the sensor signal to the processing and memory circuitry by wireless or wired connection. The circuitry is configured to receive and process the sensor signal in conjunction with an executable program for analysis of data transmitted from the sensor. Data transmitted from the tag attached to the specimen container is also input to the processing and memory circuitry by wireless or wired connection from the reader. The circuitry in conjunction with an executable program for analysis of data determines whether the specimen complies with the order for the specimen. The circuitry is further configured to present a signal to a user indicating that the specimen complies with the specimen order or is inadequate to do so. A signal presented to a user may be in the form of a text message on a display, colored and/or flashing light, on a reader display. In addition a reader may present a signal in the form of an audio cue, such as a warning tone.

In a preferred option, the sensor is adapted to measure the quantity of a specimen in a specimen container. In a further preferred option the specimen sensor is a weight sensor adapted to sense the weight of the sample container and to transmit the weight sensor signal to the processing and memory circuitry by wireless or wired connection. The circuitry is configured to receive and process the weight sensor signal in conjunction with an executable program for analysis of data transmitted from the sensor. Data transmitted from the RFID tag attached to the specimen container is also input to the processing and memory circuitry by wireless or wired connection from the reader. The circuitry, in conjunction with an executable program for analysis of data is configured to determine the weight of a specimen in the specimen container and to determine whether the specimen weight is sufficient to comply with the order for the specimen. Information transmitted from the tag indicative of the type of container allows lookup of empty container weight optionally stored in memory such that a comparison of the current weight measurement of the filled specimen container with the reference unfilled weight measurement results in specimen weight. As noted above, reference container weight may also be stored as information contained in the tag memory and transmitted to the reader for input to a processor. The circuitry is further configured to present a signal to a user indicating that the amount of specimen present in the container is adequate to comply with the specimen order and thus to confirm compliance with the specimen order. In addition, the reader is configured to present a signal to a user indicating that the amount of specimen present in the container is inadequate to comply with the specimen order. A signal presented to a user may be in the form of a text message on a display, colored and/or flashing light, on a reader display. In addition a reader may present a signal in the form of an audio cue, such as a warning tone.

Optionally, a specimen sensor is an opacity sensor. An opacity sensor is preferably attached to the specimen container holder receptacle such that when the container is properly filled and inserted in the receptacle, a sensor signal is sent to the processor is processed such that proper filling is detected and a confirmatory signal is presented to a user. Thus, for example an opacity sensor may be placed at a particular height on a wall of a receptacle such that a change in opacity of the specimen container resulting from filling the container with specimen at or above the height on the receptacle wall indicates sufficient volume of specimen in the container to comply with the specimen order.

Following confirmation of a properly obtained specimen, instructions are optionally displayed for collection of a further specimen where one has been ordered.

FIG. 1 depicts an embodiment of an inventive system 10 including a specimen holder 12 having a receptacle 14 for removably receiving a specimen container 16, the specimen container having a machine readable wireless identification tag 18 attached thereto. Further shown is a device 20 having a visual display screen and including a radio frequency identification reader configured to interrogate the tag 24 and receive information from the tag 22 identifying a specimen container characteristic. Also shown are various control and display buttons on the face of the device 20. Optionally, an inventive system further includes a specimen sensor 26 in sensing communication with the receptacle 14. The specimen sensor 26 is in data communication 28 with processing and memory circuitry incorporated in device 20.

Figure 2:
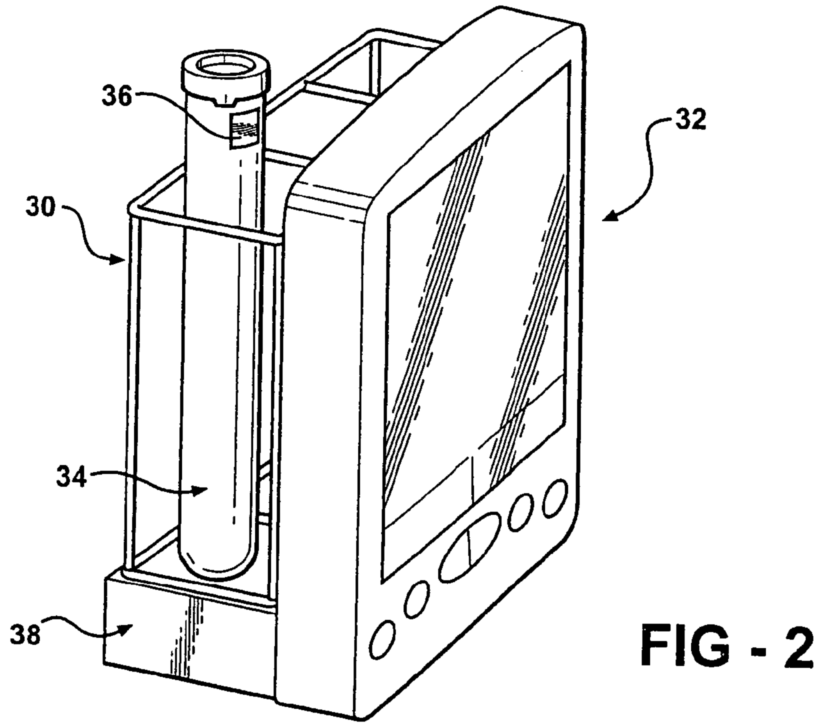
FIG. 2 is a drawing illustrating an embodiment of the invention.

FIG. 2 depicts an embodiment of an inventive system in which the specimen holder 30 is attached to the device 32, the device including processing and memory circuitry and having a visual display. FIG. 2 further illustrates a specimen container 34 having a machine readable wireless tag 36 attached thereto. Also shown is a specimen sensor 38.

Figure 3:
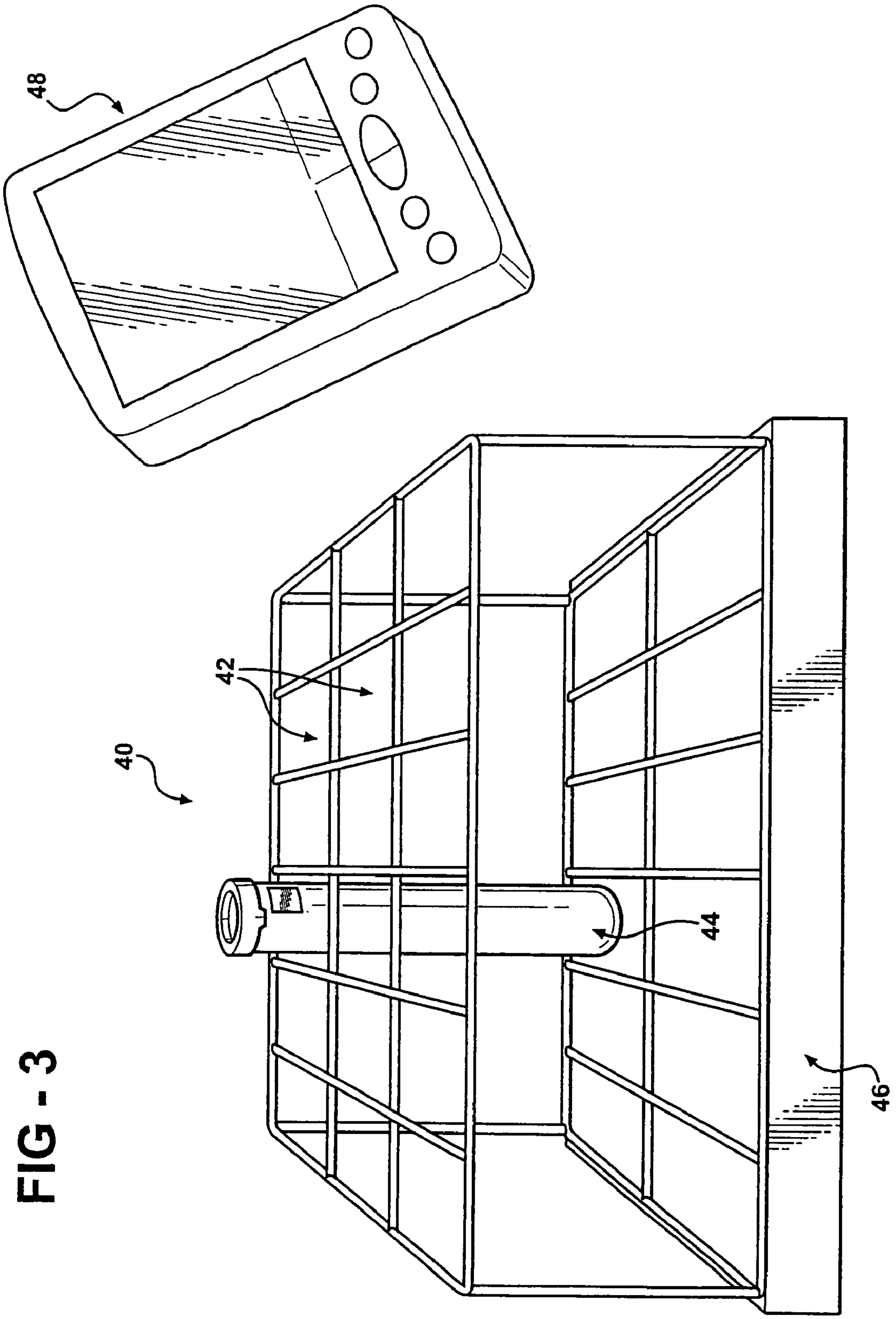
FIG. 3 is a drawing illustrating an embodiment of the invention.

In another embodiment of an inventive system, a plurality of receptacles is included in a specimen holder. For example, as shown in FIG. 3, an inventive system 40 includes a plurality of receptacles 42 for receiving a specimen container such as shown at 44. A specimen sensor 46 is shown which is in data communication a reader 48.

While the specimen holder illustrated is shown in the form of a "wire" tube rack, it is appreciated that a holder may include further structure for support of a specimen container. For example, the holder may be configured to include one or more walls extending from the top of the rack to the base or to a position between the top and base. In addition, dividers defining each receptacle may be lengthened to extend from the top of the rack to the base or to a position between the top and base. A specimen holder is formed from any durable material compatible with carrying and protecting a specimen container. Typical materials include a durable metal such as steel and a synthetic or natural polymer such as polycarbonate. In addition, an inner surface of a receptacle may be lined with a shock-absorbing material for protection of the specimen container.

Inventive methods for monitoring compliance with an order for a specimen are provided. An embodiment of an inventive method includes the steps of providing a system as described herein, such as a system including a specimen container having an attached machine readable wireless tag having specimen container characteristic information; a specimen container holder having a receptacle for removably receiving a specimen container; a device having data input and output capacity, processing circuitry, memory circuitry and an executable program for analysis of data transmitted from the tag and/or the sensor; a radio frequency identification reader in data communication with the tag and the device; a display disposed on the device or the reader; and an optional sensor for measuring a quantity of a patient specimen, the sensor disposed in contact with the receptacle, the sensor in data transmission communication with the device.

A further step includes placing an order for a patient specimen, the order having specific requirements that must be met in order to comply with the order. For example, an order will often require use of a specific type of specimen container as well as a sufficient quantity of the patient specimen in order to comply with the order.

The technician provides an input to the system indicating that the specimen is about to be obtained. For instance, the input may be typing the patient's name for entry into the system, clicking on a task name on an itemized task list presented on the display and the like. This input directs retrieval of one or more requirements to be fulfilled in order to comply with the order.

A requirement common to all orders for a patient specimen is that the specimen be obtained from the correct individual. A step included in an inventive method is confirmation that the patient from whom the specimen is obtained is the patient for whom the order for the patient specimen is given. In a preferred option, an inventive system includes a patient identification badge, such as a wristband, having an attached RFID tag containing identification information associated with the patient. In a preferred optional step, an RFID reader is activated to read an RFID tag attached to a patient identification badge. Information transmitted from the tag activates a display indicating that the patient is or is not the patient for whom the order for a specimen was given.

A radio frequency reader is activated to read information contained in a radio frequency identification tag attached to a specimen container chosen by a technician in preparation for obtaining the required specimen. The tag signal is communicated to processing and memory circuitry in the device and an executable program for analysis of data transmitted from the tag is implemented comparing tag information indicative of the type of container to which the tag is attached with a requirement of the order for a specific container type. The processing results in activation of a first signal presented to the technician by a display indicative of confirmation that the selected container having the tag read by the reader is suitable for use in complying with the order, or alternatively, that the container selected is not suitable. Optionally, instructions for further action by the technician are displayed. The technician perceives the first signal and acts accordingly, obtaining the specimen or choosing another container and repeating the steps of reading the tag and perceiving the signal until a confirmation that the chosen container complies with the requirements of the order is displayed by the display.

In addition to requiring a particular type of container, the order may require a plurality of containers. A process analogous to the above-described process for choosing the correct type of container may be implemented to assure that the correct number of containers is selected.

Having obtained confirmation that the number and type of containers selected fulfills the requirements of the order, the technician obtains the specimen and places the specimen in the specimen container or containers. In a preferred option, the technician then reads the tag attached to each specimen container containing a specimen and inputs information to the system indicating that the specimen has been obtained. The reader transmits the information to processing and memory circuitry to create a record that the specimen has been obtained and additionally to indicate that the unique identification number included in the tag is now associated with the patient's specimen.

In an embodiment of the present invention in which a sensor for use in measuring a quantity of a specimen in a specimen container is included, a further step of an inventive method includes placing the specimen container containing a quantity of a specimen in a receptacle of the specimen container holder having a sensor for measuring the quantity of the patient specimen disposed thereon. Sensor information indicating that a quantity of the specimen is present in the container is transmitted to processing and memory circuitry to compare the quantity of the specimen in the container with the quantity of specimen required in order to comply with the order. If the quantity in the container is sufficient to comply with the order, a second signal is activated and presented by a display indicating this information to the technician. Alternatively, if the quantity in the container is insufficient to comply with the order, the second signal is activated and presented by the display to so indicate to the technician. The technician perceives the second signal and acts accordingly, accepting the specimen as fulfilling the order requirement or obtaining a further quantity of specimen and repeating the steps inserting the specimen container with specimen in the receptacle for measurement by the sensor and perceiving the signal until a confirmation that the quantity of specimen obtained complies with the requirements of the order is displayed by the display. Optionally, further instructions for technician action are provided and presented on the display.

Further steps of an inventive process include inputting an indicator that the patient specimen required by the order has been obtained. For example, a technician may push a button operative to send such an indication to system processor and/or memory. A further step includes activating the radio frequency reader to read the tag attached to the specimen container, the tag containing information indicative of a unique container identifier and transmitting the information to the device processor and memory circuitry. The unique container identifier information is optionally associated with the indicator that the patient specimen has been obtained such that inquiry into entries associated with the order will indicate the specific tube containing a specimen that complies with the order.

Any patents or publications mentioned in this specification are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The apparatus and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A system for monitoring compliance with an order for a specimen, comprising:

- a specimen container comprising a machine readable wireless tag; the tag containing specimen container characteristic information;
- a device having data input and output capacity, processing circuitry, memory circuitry and an executable program for analysis of data transmitted from the tag;
- a machine readable wireless reader in data communication with the tag and the device;
- a display disposed on the device or the reader, wherein said specimen container characteristic information is selected from the group consisting of: a specimen container type, container identification information, weight of the container when empty, weight of the container containing a volume of specimen, opacity of the container and opacity of the container containing a volume of specimen;

wherein the specimen container characteristic information further comprises patient identification information identifying a patient whose specimen is to be contained in the specimen container, a test to be performed on the specimen, or an amount of specimen required; and wherein said system further comprises a patient identification badge having an attached radio frequency identification tag operable with said wireless reader.

2. The system of claim 1 wherein the reader is disposed on the device.

3. The system of claim 1 wherein the tag is selected from the group consisting of: passive, active, read-only and read-write.

4. The system of claim 1 wherein the device is selected from the group consisting of: a personal digital assistant, a personal computer a mainframe and a server.

5. The system of claim 1 wherein the display is selected from the group consisting of: a display screen, a light signal emitter, and an acoustic signal emitter.

6. The system of claim 1 further comprising a specimen container holder having a receptacle for removably receiving the specimen container.

7. The system of claim 6 further comprising a sensor disposed in contact with the receptacle, the sensor in data transmission communication with the device.

8. The system of claim 7 wherein the sensor is a weight sensor.

9. The system of claim 7 wherein the sensor is an opacity sensor.

10. The system of claim 7 wherein the device further comprises an executable program for analysis of data transmitted from the sensor.

11. The system of claim 10 wherein the radio frequency identification reader is disposed on the holder.

12. The system of claim 10 wherein the device having data input and output capacity, processing circuitry, memory circuitry and an executable program for analysis of data transmitted from the tag is disposed on the holder.

13. A method for monitoring compliance with an order for a specimen, comprising the steps of:

providing a system according to claim 1;

inputting an order for a patient specimen to the memory, the order requiring use of a first type of specimen container in order to comply with the order;

selecting a specimen container;

activating a wireless machine reader to read the tag attached to the specimen container, the tag containing information indicative of the container type;

transmitting the information contained in the tag from the reader to the device;

retrieving the record of the order for a patient specimen requiring use of the first type of specimen container;

comparing the information contained in the tag read by the reader identifying the container type with the container type required by the order to determine whether the container having the attached tag read by the reader is the first type of specimen container required in order to comply with the order; and presenting information on the display indicating whether the specimen container having the attached tag read by the reader is the first type of specimen container required in order to comply with the order, thereby monitoring compliance with an order for a specimen.

14. The process of claim 13 further comprising the step of confirming the identity of the patient as a patient for whom the order for a patient specimen was placed.

15. A method for monitoring compliance with an order for a specimen, comprising the steps of:

providing a system according to claim 7;

inputting an order for a patient specimen to the memory, the order requiring a specified quantity of a patient specimen in order to comply with the order;

obtaining a quantity of the patient specimen from a patient;

introducing the quantity of the specimen in the specimen container;

placing the specimen container in a receptacle of the specimen container holder, the receptacle having a sensor for measuring the quantity of the patient specimen disposed thereon;

transmitting a sensor signal from the sensor to the device having data input and output capacity, processing circuitry, memory circuitry and an executable program for analysis of data transmitted from the sensor;

retrieving the record of the order for a patient specimen requiring the specified quantity of a patient specimen in order to comply with the order;

comparing the signal transmitted by the sensor indicative of the quantity of specimen in the container with the specified quantity of a patient specimen required by the order to determine whether the quantity of specimen in the container is sufficient in order to comply with the order; and presenting information on the display indicating whether the quantity of specimen in the container is sufficient in order to comply with the order, thereby monitoring compliance with an order for a specimen.

16. The process of claim 15 further comprising the step of confirming the identity of the patient as a patient for whom the order for a patient specimen was placed.

17. The process of claim 15 further comprising the steps of:

inputting an indicator that the patient specimen required by the order has been obtained;

activating the radio frequency reader to read the tag attached to the specimen container, the tag containing information indicative of a unique container identifier;

transmitting the information to the memory; and associating the information with the indicator that the patient specimen has been obtained.

* * * * *